United States Patent
Merlob

(10) Patent No.: US 9,869,602 B2
(45) Date of Patent: Jan. 16, 2018

(54) PIPELINE LEAK DETECTION DEVICE AND METHOD

(71) Applicant: Darren E. Merlob, Calabasas, CA (US)

(72) Inventor: Darren E. Merlob, Calabasas, CA (US)

(*) Notice: Subject to any disclaimer, the term of this patent is extended or adjusted under 35 U.S.C. 154(b) by 206 days.

(21) Appl. No.: 14/572,259

(22) Filed: Dec. 16, 2014

(65) Prior Publication Data
US 2015/0198497 A1  Jul. 16, 2015

Related U.S. Application Data

(60) Provisional application No. 61/927,777, filed on Jan. 15, 2014.

(51) Int. Cl.
| | |
|---|---|
| G01M 3/24 | (2006.01) |
| G01M 3/00 | (2006.01) |
| F16L 55/26 | (2006.01) |
| F17D 5/06 | (2006.01) |
| G01N 29/14 | (2006.01) |
| G01N 29/265 | (2006.01) |
| G01N 29/04 | (2006.01) |

(52) U.S. Cl.
CPC .............. *G01M 3/00* (2013.01); *F16L 55/26* (2013.01); *F17D 5/06* (2013.01); *G01M 3/005* (2013.01); *G01M 3/246* (2013.01); *G01N 29/04* (2013.01); *G01N 29/14* (2013.01); *G01N 29/265* (2013.01); *G01N 2291/2636* (2013.01)

(58) Field of Classification Search
CPC ........ G01M 3/00; G01M 3/246; G01M 3/005; G01N 29/04; G01N 29/265; G01N 29/14; G01N 2291/2636; F17D 5/06; F16L 55/26

USPC .......................................................... 73/592
See application file for complete search history.

(56) References Cited

U.S. PATENT DOCUMENTS

| | | | | |
|---|---|---|---|---|
| 5,027,644 | A * | 7/1991 | Ziolkowski | G01M 3/246 137/505.37 |
| 5,038,614 | A * | 8/1991 | Bseisu | G01N 29/07 376/252 |
| 5,907,100 | A * | 5/1999 | Cook | G01N 29/2412 73/602 |
| 5,963,042 | A * | 10/1999 | Suyama | G01N 22/02 324/326 |
| 5,974,862 | A * | 11/1999 | Lander | G01M 3/243 702/51 |
| 6,005,396 | A * | 12/1999 | Suyama | G01N 22/02 324/528 |
| 6,351,985 | B1 * | 3/2002 | Bedwell | G01M 3/2853 138/90 |

(Continued)

*Primary Examiner* — J M Saint Surin
(74) *Attorney, Agent, or Firm* — Fulwider Patton LLP

(57) ABSTRACT

A pipeline leak detection device for detecting leaks in a pipe includes a sensor assembly guided into a pipe to detect evidence of a leak, and a position assessing device provides an indication of a location of the sensor assembly. The sensor assembly may be a hydrophone, and the position assessing device may be a guide wire with markings for measuring lengths of the guide wire, or a transmitter. An injector plug can be inserted in an access port of the pipe to create a liquid tight seal for insertion of the sensor assembly. A pressurizing device may also be connected to the access port to pressurize the pipe.

13 Claims, 3 Drawing Sheets

(56) References Cited

U.S. PATENT DOCUMENTS 6,567,006 B1 * 5/2003 Lander ................ G01M 3/243
340/605
2010/0156632 A1 * 6/2010 Hyland ................ G08B 25/08
340/540

* cited by examiner

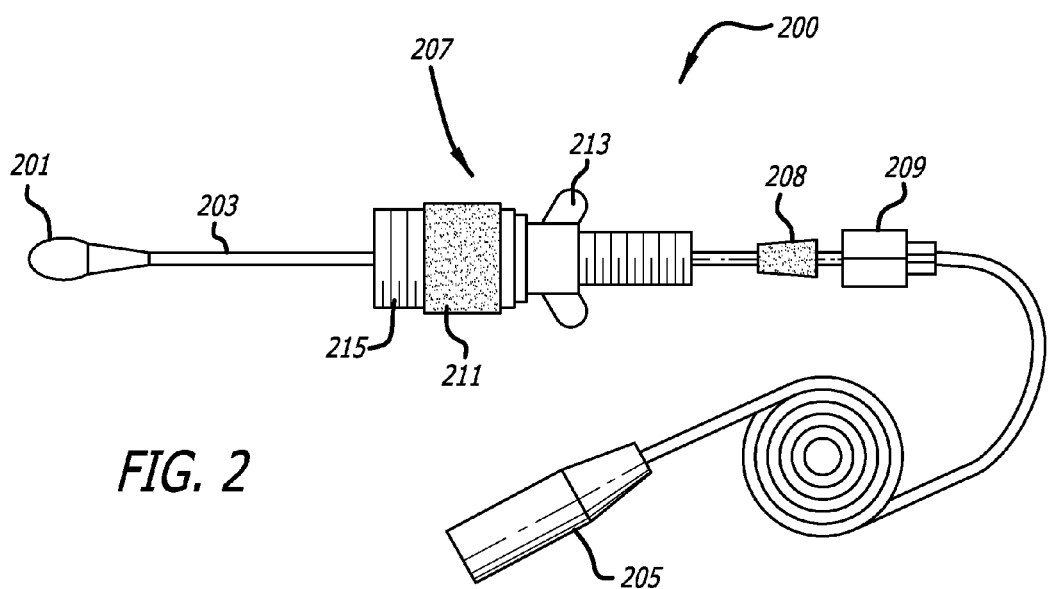
FIG. 2
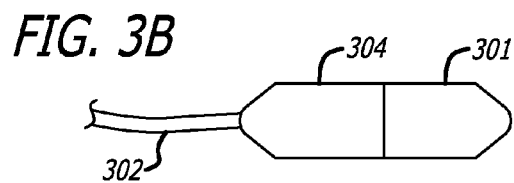
FIG. 3B
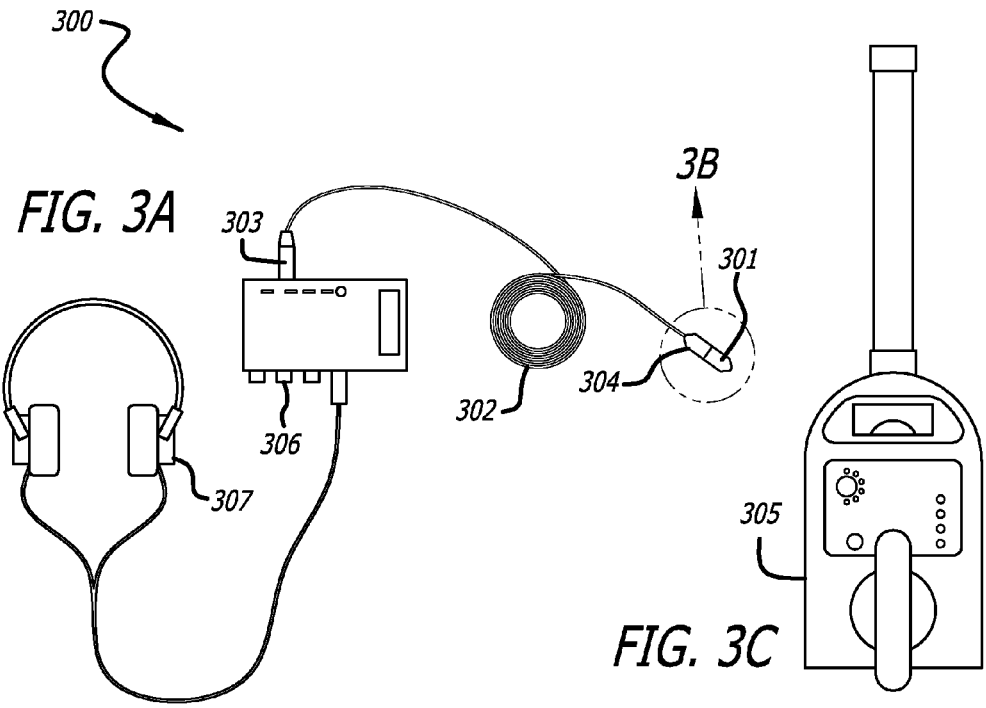
FIG. 3A
FIG. 3C

PIPELINE LEAK DETECTION DEVICE AND METHOD

CROSS-REFERENCES TO RELATED APPLICATIONS

This application is based upon and claims priority from U.S. Application No. 61/927,777, filed Jan. 15, 2014, incorporated by reference in its entirety.

BACKGROUND

The present invention relates to a pipeline leak detection device, system, and method for detecting leaks in plumbing. An important part of repairing leaks in plumbing is locating damaged pipes. One common method of identifying a leak is by visually inspecting the plumbing line. A person looking for a leak may search for telltale signs of structural damage such as dripping liquid, cracks, dents, and the like.

However, plumbing is often a complicated maze that is hidden from view. In some cases, plumbing may be hidden within a wall, above a ceiling, under the floor, or underground. In some cases, a person may be able to identify the location of a damaged pipe from seeing discoloration of the surrounding area, pooling liquid, and/or dripping liquid.

Other times, these signs may not exist or may be deceptive. For example, a pool of liquid may form at a different location than the damaged plumbing due to an incline, or there may be multiple leaks causing a single liquid pool. In these cases, someone will have to remove all of the obstructions to locate and repair the damaged plumbing. In cases where the plumbing line is a gas line, leaks may be invisible, and the only evidence of a leak may be damage to the pipes.

There are several other ways that plumbers can locate leaks. In one example, plumbers may use dyes in different plumbing lines to determine which line has a leak; the dye for the leaky plumbing line will match the color of the leak. Another common method is to trace an obstructed pipeline with a stethoscope while listening for audible leak indicators. However, using a stethoscope is fairly inaccurate and may not work for quieter leaks or pipelines that are several feet underground. Sometimes a leak is at the top of a pipeline bend, and only leaks during certain events, such as a flush of a toilet. These types of leaks are difficult to listen for because they are not always leaking. Furthermore, these and other common methods of detecting leaks are extremely inexact. Having inaccurate methods of locating leaks will often require excavation and property destruction for identification of damaged pipes.

Thus, it would be preferable for there to be a more accurate and efficient way of locating leaks in malfunctioning pipes. The present invention meets these and other needs.

SUMMARY OF THE INVENTION

In the most general aspect of the present invention, a pipeline leak detection device, system, and method for detecting leaks in plumbing or pipes are disclosed. In one aspect, a guiding device can be used to navigate or guide a sensor assembly within a pipeline to a location of a leak for detecting evidence of the leak. In another aspect, the guiding device can provide an indication of the location of the sensor assembly. In one aspect, the location of the sensor assembly can be determined from an electromagnetic signal. In another aspect, the location of the sensor assembly also can be determined from distance measurements of how far the sensor assembly has traveled. In another aspect, pressure can be added into the pipeline in order to aid the sensor assembly in detecting indications of a leak. In another aspect, a hose connects a pressurizing device to a pipe through an access port so that the pressurizing device can provide pressure within the pipe, and the sensor assembly is configured to be inserted into the pipe through the access port to detect vibrations of a leak in the pipe. In one presently preferred aspect, the hose has a pressure gauge that displays the pressure within the pipe. In another aspect, the hose has a valve for controlling the pressure within the pipe. In another aspect, the pressurizing device may a water faucet, compressor, or a pressure rig, for example. The sensor assembly is guided to the location of the leak and the location of the leak is determined by the location of the sensor assembly.

In another aspect of the invention, a sensor assembly is configured to be inserted into a pipe to detect vibrations caused by a leak within the pipe, and is configured to provide an indication of the amplitude of the vibration, and the sensor assembly preferably is connected to a position locating or position assessing device configured to provide an indication of the location of the sensor assembly. In yet another aspect, a headphone is configured to receive audio signals from the sensor assembly. In still another aspect, the sensor assembly may include a hydrophone. In another aspect, an electromagnetic transmitter is attached to the sensor assembly and is configured to provide an indication of the location of the transmitter to a receiver.

In yet another aspect, the guiding device such as a guide wire or line is connected to the sensor assembly, and the guide wire or line is configured to provide an indication of a location of the sensor assembly. In another aspect, the guide wire or line is threaded through an injector plug that is configured to create a liquid tight seal to an access port of a pipe.

The present invention accordingly provides for a pipeline leak detection device for detecting leaks in a pipe, including a sensor assembly configured to be inserted in a pipe to detect vibrations caused by a leak within the pipe, and to provide an indication of an amplitude of the vibrations. A position assessing device configured to provide an indication of a location of the sensor assembly preferably is also connected to the sensor assembly. In one presently preferred aspect, the sensor assembly may include a hydrophone.

In another presently preferred aspect, the position assessing device connected to the sensor assembly includes a guiding device, such as a guide wire or line, for example, that can be configured to carry an electrical wire connected to the sensor assembly. In another presently preferred aspect, an injector plug is provided that is configured to be received in an access port of the pipe to create a liquid tight seal to the access port of the pipe, and the guide wire or line is configured to be threaded through the injector plug. In another presently preferred aspect, a headphone may also be provided to receive audio signals from the sensor assembly through the electrical wire. In another presently preferred aspect, an electromagnetic transmitter configured to provide an indication of the location of the transmitter to a receiver may be attached to the sensor assembly.

The present invention also provides for a system for detecting leaks in a pipe having an access port, including a hose connecting a pressurizing device connected to the access port of the pipe to provide pressure within the pipe through the access port, a sensor assembly configured to be inserted in the pipe to detect vibrations of a leak in the pipe, and a guiding device connected to the sensor assembly to guide the sensor assembly until the vibrations detected by the sensor assembly from the leak are at a maximum. A position locating device configured to determine a location of the sensor assembly preferably also is connected to the sensor assembly. In a presently preferred aspect, the hose includes a pressure gauge that displays the pressure within the pipe. In another presently preferred aspect, the hose includes a valve for controlling the pressure within the pipe. In another presently preferred aspect, the pressurizing device is a water faucet. In another presently preferred aspect, the pressurizing device is a compressor. In another presently preferred aspect, the pressurizing device is a pressure rig. In another presently preferred aspect, an electromagnetic transmitter is attached to the sensor assembly and is configured to provide an indication of a location of the transmitter.

The present invention also provides for a method of detecting leaks in a pipe. In the method, a sensor assembly configured to detect vibrations caused by a leak is inserted into the pipe, the sensor assembly is guided to a location within the pipe where the vibrations detected by the sensor assembly are at a maximum, and a location of the sensor assembly where the vibrations detected by the sensor assembly is at a maximum is determined. In a presently preferred aspect, a guide wire or line connected to the sensor assembly is pushed into the pipe, and a location of the sensor assembly can be determined by measuring a length of the guide wire or line inserted in the pipe. In another presently preferred aspect, a location of the sensor assembly can be determined by an electromagnetic signal transmitter attached to the sensor assembly with a receiver. In another presently preferred aspect, pressure is added within the pipe, such as by connecting a pressure rig to the pipe, for example.

These and other features and advantages of the present invention will become more apparent from the following detailed description of the preferred embodiments in conjunction with the accompanying drawings, which illustrate, by way of example, the operation of the invention.

BRIEF DESCRIPTION OF THE DRAWINGS

FIG. 2 is a schematic diagram illustrating an exemplary pipeline leak detection device for detecting the location of leaks in a pipeline, according to the present invention.

FIG. 3A is a schematic diagram illustrating an alternative exemplary pipeline leak detection device for detecting locations of a leak in a pipeline, according to the present invention.

FIG. 3B is an enlarged view of the microphone, transmitter, and a portion of the line of the pipeline leak detection device of FIG. 3A.

FIG. 3C is a top plan view of a receiver 305 for receiving an electromagnetic signal from the transmitter of the pipeline leak detection device of FIG. 3A.

DETAILED DESCRIPTION OF THE PREFERRED EMBODIMENTS

As will be described hereinafter in greater detail, the various embodiments of the present invention relate to a pipeline leak detection device, system, and method for detecting leaks in a pipe, such as a plumbing pipeline, for example. For purposes of explanation, specific nomenclature is set forth to provide a thorough understanding of the present invention. Description of specific applications and methods are provided only as examples. Various modifications to the embodiments will be readily apparent to those skilled in the art, and the general principles defined herein may be applied to other embodiments and applications without departing from the spirit and scope of the invention. Thus the present invention is not intended to be limited to the embodiments shown, but is to be accorded the widest scope consistent with the principles and steps disclosed herein.

Many pipeline leaks provide signs that are detectable from inside the pipeline. As an example, but not by way of limitation, one of these indicators is an audible sound, such as a hiss. This is especially true for leaks in pressurized pipes. One may be able to locate a leak by using a sensor assembly to find the audible sound of the hiss. In another method, a sensor assembly may be configured to find visual or other indications of a leak to aid in locating a leak. For example, some other indicators of a leak may include, but are not limited to, vibrations in the pipes and/or the containing liquid or gas. A sensor assembly configured to detect these vibrations and/or sounds can help identify and locate the corresponding leaks. In one embodiment, a sensor assembly may be configured to search for evidence of a leak, such as one or more audible, visible, or otherwise detectable leak cues. In a presently preferred aspect, the sensor assembly includes one or more sensors or detectors for detecting evidence of leaks.

Figure 1:
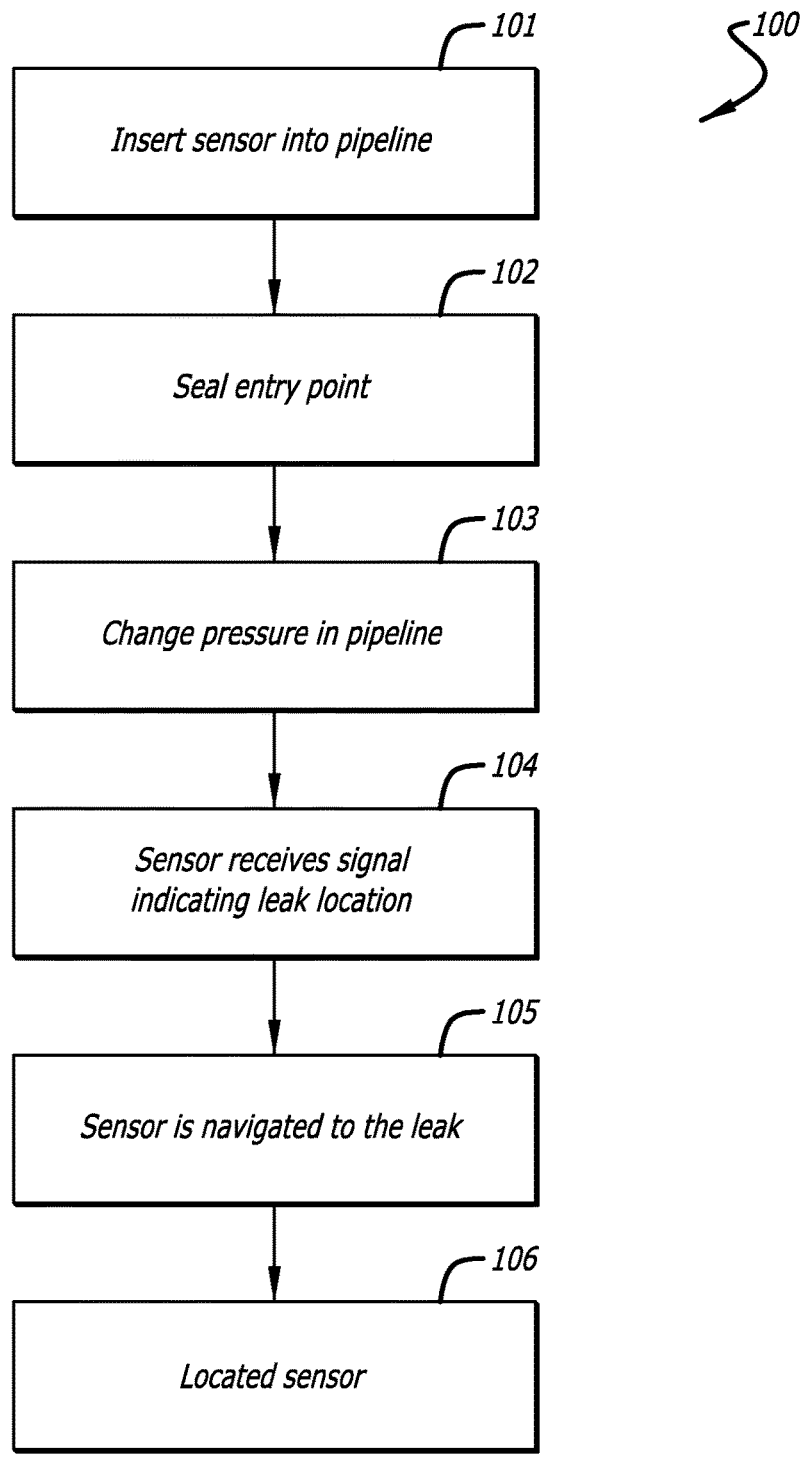
FIG. 1 is a flow chart illustrating an exemplary method for detecting the location of leaks in a pipe, according to the present invention.

Referring to FIG. 1, in an exemplary method for detecting leaks 100 according to one embodiment, at step 101 a user may insert a sensor assembly for leak detection within a leaky pipeline. The sensor assembly may include one or more audio sensors, visual sensors, pressure sensors, and combinations thereof, and the like. The sensor assembly may be wired or wireless. There may be an access port, a drain hole, or other opening for inserting the sensor assembly. Some pipelines have resealable access ports that a user may use as an entry point. In other instances, a user may have to create an opening in the pipeline for inserting the sensor assembly. Creating an opening may require drilling or cutting a portion of the pipeline.

At step 102 the user optionally may seal the access port, a drain hole, or opening that the sensor assembly is using for access. According to one embodiment, the access port, a drain hole, or opening may be sealed by a plug. The plug may be an injector plug that allows for a guide line to guide or manipulate the sensor assembly in a pipeline through the plug, yet still maintain a watertight or airtight seal. In an alternative method, the access port, a drain hole, or opening may remain unsealed.

At step 103, liquid or gas pressure optionally may be added within the pipeline. In one embodiment, a pressure rig, compressor, or a faucet may add pressure to the pipeline through the access port, a drain hole, or opening. A hose may connect the pressure rig, compressor, or faucet to the access port, a drain hole, or opening. The hose may have a pressure gauge for measuring the pressure in the pipeline, and a valve for controlling pressure in the pipeline. In cases of detecting sound waves caused by a water leak, a pressure in a range of about 3 to 10 psi tends to provide the most detectable sound for a microphone, such as a hydrophone particularly suited to detect sound in or through water, for example. The best pressure range for liquids tends to be a range of about 6 to 10 psi. In the case of detecting gas leaks, pressure range of about 8 to 15 psi provides the most detectable sound. In one embodiment, the hose, pressure rig, compressor, or faucet may have a pressure regulator that automatically maintains a certain pressure level in the pipeline. A user may be able to set the desired pressure level with the pressure regulator.

At step 104 the sensor assembly detects evidence for locating a leak. For example, in one embodiment, the sensor assembly can detect audible sound waves or inaudible vibrations conducted through liquid or gas within a pipeline, and can be used to determine a direction from which such audible sound waves or inaudible vibrations caused by the leak are coming, such as by determining and comparing the strength of the vibrations at various locations along the pipeline. For example, assuming the sensor assembly is detecting sound waves, the sensor assembly may identify the direction of the leak by the changes in amplitude or volume of the sound waves when the sensor assembly moves closer or farther away from a leak.

At step 105, a user may navigate or guide the sensor assembly into the pipeline until the sensor assembly is at a point where the detected vibrations are at a maximum (where the leak is most likely located). In one instance, a navigating or guiding device such as a guide wire or line may be used to navigate or guide the sensor assembly to the location of the leak. In alternative embodiments, the sensor assembly may be attached to a mobile vehicle that brings the sensor assembly to the location of the leak. The mobile vehicle may be remote controlled or self-guiding. A self-guided mobile vehicle may navigate or guide itself to the location of a leak using signals received from an attached sensor assembly. The mobile vehicle may be programmed to home in on a particular signal that the sensor assembly detects, for example.

At step 106, a mechanism may determine the location of the sensor assembly, thereby determining the location of the leak. According to one embodiment, the mechanism may be an apparatus for determining a distance measurement of how far the sensor assembly traveled. For example, if a guide wire or line pushed the sensor assembly to a location of a leak, the length of the guide wire or line could be measured. The guide wire or line itself may have measurement markings to aid a user in identifying the location of the sensor assembly.

In an alternative embodiment, the sensor assembly may be attached to or include a position locating or position assessing device that sends out a signal, such as an electromagnetic signal, providing an indication of its location. In one embodiment, the sensor assembly may be a sonde, capable of monitoring multiple physical parameters, and including a position locating or position assessing device, for example. In another embodiment, the position locating or position assessing device may be a GPS (Global Positioning System) device that transmits its own GPS coordinates. Signals from the position locating or position assessing device may be transmitted through wired or wireless communications. Wireless communication may include wifi, Bluetooth, SMS, and/or other wireless communication systems. One embodiment may use a mobile phone network for wireless communications.

In yet another embodiment, the position locating or position assessing device may send out an electromagnetic signal, so that a receiver can detect the location of the position locating or position assessing through the strength of the electromagnetic signal. In another embodiment, a receiver may locate the position locating or position assessing device through wireless signal ping, and calculate the distance between the receiver and the position locating or position assessing device from the ping time. In yet another embodiment, the receiver may use a system that triangulates the location of the signal that the position locating or position assessing device emits.

In yet another alternative embodiment, the sensor assembly may be attached to a mapping device that records or detects the movement of the sensor assembly and maps the movement of the sensor assembly. This data may be transferred to a computing device through a wired or wireless communicator. One of ordinary skill in the art would recognize other methods of determining a sensor assembly's location, all of which are contemplated herein.

FIG. 2 is an illustration of an exemplary leak detection device 200 according to an embodiment of the present invention. Leak detection device 200 may include a sound detector for converting sound waves into electrical signals, such as microphone 201. Microphone 201 may be a standard microphone, or it may be a microphone specifically designed for the acoustic impedances that may exist within the plumbing pipes. Microphone 201 may be a hydrophone, which is configured to detect audio signals underwater, and may be a directional hydrophone, for example.

Microphone 201 may transmit the electrical signal to one or more of a speaker, amplifier, recording device, sound wave viewer, computing device, amplitude display, or the like, for example. The electrical signal may be transmitted through a wire or wireless communicator. Microphone 201 may include an analog to digital converter for converting electrical signals caused by sound waves into a digital signal for wireless transmission.

Microphone 201 may be attached to a guiding device, such as a guide wire or line 203. Line 203 may be made of a flexible material, but line 203 may also be of sufficient stiffness so that line 203 may be easily fed through twists and turns of a pipeline. According to one embodiment, line 203 may have flexibility similar to that of a drain snake.

Line 203 may also be configured to have a waterproof cavity to carry an electrical wire from microphone 201 on one end of line 203 to a microphone connector 205 on another end of line 203. Line 203 may also be configured to carry multiple electrical wires. In an alternative embodiment, microphone 201 may be a wireless microphone that is battery powered. In this alternative embodiment, line 203 may lack a cavity for carrying internal electrical wires. Microphone connector 205 may plug into an amplifier connected to headphones, to allow a user to listen to the audio signals that microphone 201 picks up. In this manner, a user may be able to guide the microphone to a leak by navigating or guiding microphone 201 to where the audio signal of the leak is at a maximum. Alternatively, microphone connector 205 may be connected to a signal strength viewing device that displays the amplitude of the signal from microphone 201. A user may be able to guide the microphone to a leak by guiding microphone 201 in a direction that increases the amplitude of the sound wave signal picked up by the microphone. Alternatively, a computer programmed vehicle may be configured to guide a microphone towards the increasing amplitude picked up by the microphone.

In one alternative embodiment, guide wire or line 203 may have distance markings similar to a ruler. In this manner, a user may be able to determine how far the microphone has been fed into a pipeline. A user may feed the microphone into a pipeline until the user pinpoints a leak in the pipeline and use the distance markings to help approximate where the leak is located in a pipeline, even if the pipeline is behind a wall or underground.

According to one embodiment, a spooling or coiling device may spool or release line 203. The spooling device may have a motorized unraveling device for unravelling and feeding line 203 into a pipeline. The spooling device may also have a device to retract and coil line 203. The retracting device may, for example, be a manual crank, or an automated motor, for example. The spooling device may also track the amount of line 203 that is unraveled and display a measurement of the length of the line unraveled to a user.

Plug 207 may be an injector plug which allows for line 203 to be fed into a pipeline access port while preventing gas or liquids from escaping, such as a 1.5 inch access port, for example. Plug 207 may have an opening with threads 215 for connecting to an access port. Plug 207 may also have a rubber ring 211 and/or torque wings 213 attached to the base of the plug for aiding a user in screwing plug 207 in or on an access port to a pipeline. In one embodiment, conduit reducer brushings may be attached to plug 207 as an adapter to access ports that do not match plug 207.

There may be a rubber stopper 208 that fits into plug 207 that surrounds line 203 to maintain a virtually watertight or airtight seal with the injector plug. One skilled in the art would know of alternative materials that the stopper 208 may be made of, including, but not limited to rubber or silicone, all which are contemplated herein. A lock nut 209 may screw onto injector plug 207 securing rubber stopper 208.

FIGS. 3A, 3B and 3C illustrate another exemplary embodiment of a leak detection device 300. Leak detection device may have a microphone 301, line 302, and microphone connector 303 similar to leak detection device 200 in FIG. 2. Leak detection device 300 may also have a transmitter 304 that is attached to line 302 that is next to microphone 301.

Transmitter 304 may be configured to send out an electromagnetic signal that may be picked up by receiver 305. Receiver 305 also may provide an indication of the transmitter's location. In one embodiment, receiver 305 may indicate how close or far away transmitter 304 is in comparison to receiver 305 based the signal strength of transmitter 304. A lower signal strength would indicate that receiver 305 is farther away from transmitter 304. Receiver 305 may use an audio indicator, such as a beep, to indicate whether receiver 305 is closer or farther away from transmitter 304. For example, a beep may become louder as receiver 305 gets closer to transmitter 304. Alternatively the time intervals between beeps may change as the receiver comes closer to the transmitter. In yet another embodiment, a needle within a display, may indicate the distance between receiver 305 and transmitter 304. One skilled in the art would recognize other methods in which receiver 305 may provide indicators that represents the distance between transmitter 304 and receiver 305, which are contemplated herewithin.

In an alternative embodiment, transmitter 304 may be a GPS device that sends out GPS coordinates to a receiver 305. Receiver 305 may then display or provide indicators that allow a user to locate transmitter 304. Receiver 305 may display a map, coordinates, or an arrow that points towards transmitter 304, for example.

Leak detection device 300 may have an amplifier 306 to which microphone 301 is connected through a microphone connector 303. Amplifier 306 may amplify any signals microphone 301 detects and transmits the signals to headphone 307, which may also be connected to amplifier 306.

In some instances, when determining leaks with a leak detection device disclosed herein, the pressure within the pipeline may not be sufficient to create a signal detectable by the leak detection device. In these instances, an apparatus for increasing the pressure within the pipeline may be required.

Figure 4:
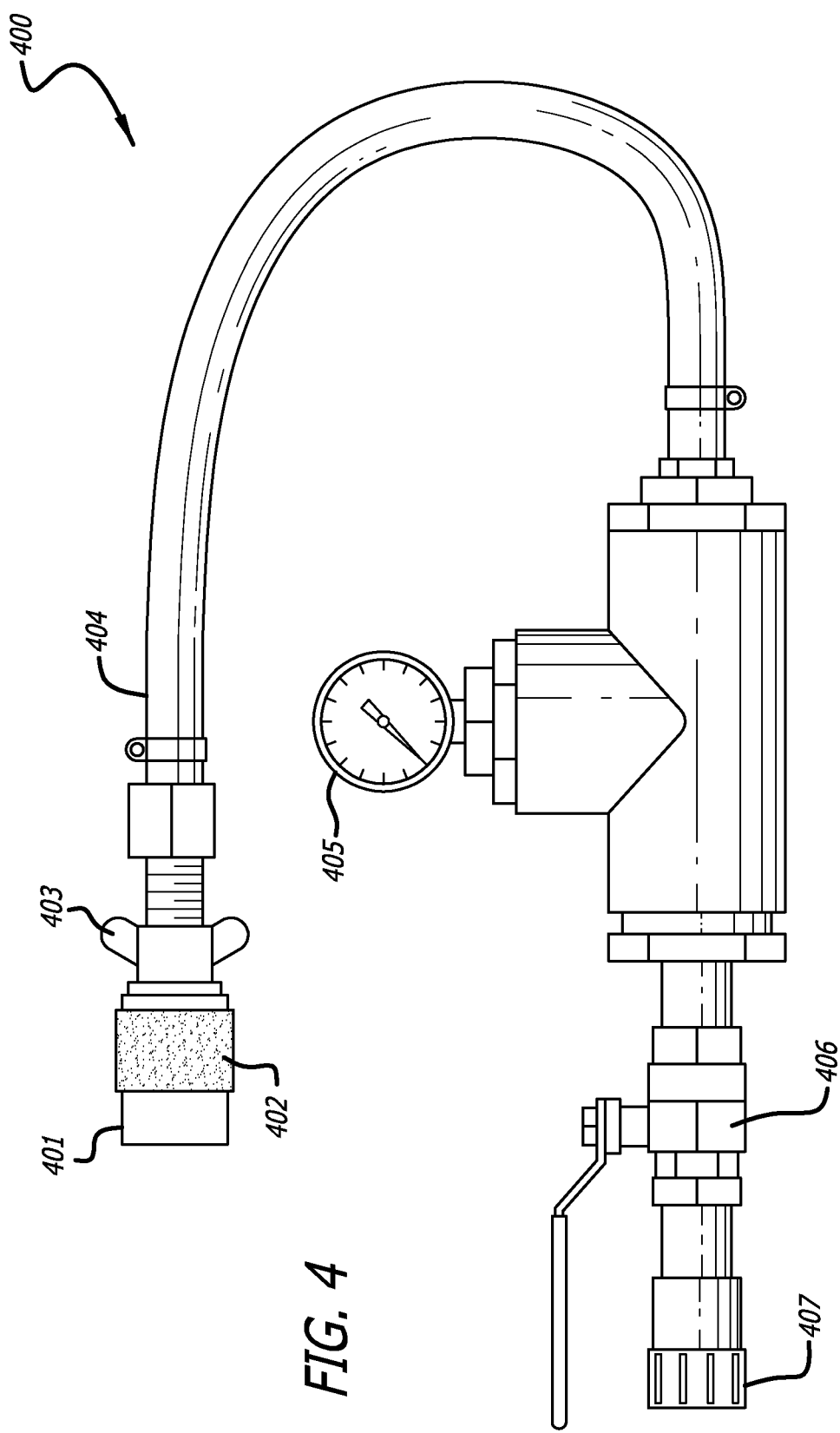
FIG. 4 is a schematic diagram illustrating an apparatus for adding pressure in a pipeline for aiding a sensor assembly of a pipeline leak detection device to detect leaks within a pipeline, according to the present invention.

FIG. 4 is an exemplary pressure connector 400 that may regulate pressure in a pipeline according to an embodiment. Pressure connector 400 may have an injector plug 401 for creating an airtight or watertight seal to an access port to the pipeline. Injector plug 401 may have a rubber ring 402 or wings 403, or both, to aid a user in screwing plug 401 into or onto an access port, for example.

Leak detection device 400 may have a hose 404 for gases or liquids to travel through and act as an extension device between a compressor, pressure rig, or faucet to a pipeline access port. Leak detection device 400 may include a pressure gauge 405 that measures and displays air or liquid pressure within the pipeline and hose 404. Leak detection device 400 may include a valve 406 which controls the amount of liquid or gas that is released into the pipeline from the compressor, pressure rig, or faucet, thereby providing control over the pressure. Leak detection device 400 maybe include a spigot connector 407 for connecting to a compressor, pressure rig, or faucet.

While particular embodiments of the present invention have been described, it should be understood that various different modifications within the scope and spirit of the invention are possible. The invention is limited only by the scope of the appended claims.

I claim:

1. A system for detecting leaks in a pipe having an access port, the system comprising:
   a hose connecting a pressurizing device connected to the access port of the pipe, the pressurizing device providing pressure within the pipe through the access port;
   a sensor assembly configured to be inserted in the pipe to detect vibrations of a leak in the pipe;
   a guiding device connected to the sensor assembly, the guiding device being configured to guide the sensor assembly until the vibrations detected by the sensor assembly from the leak are at a maximum; and
   a position locating device connected to the sensor assembly, the position locating device being configured to determine a location of the sensor assembly.

2. The system of claim 1 wherein the hose includes a pressure gauge that displays the pressure within the pipe.

3. The system of claim 2 wherein the hose includes a valve for controlling the pressure within the pipe.

4. The system of claim 3 wherein the pressurizing device is a water faucet.

5. The system of claim 3 wherein the pressurizing device is a compressor.

6. The system of claim 3 wherein the pressurizing device is a pressure rig.

7. The system of claim 3 further comprising an electromagnetic transmitter attached to the sensor assembly configured to provide an indication of a location of the transmitter.

8. A method of detecting leaks in a pipe comprising:
   inserting a sensor assembly into the pipe, the sensor assembly being configured to detect vibrations caused by a leak;
   guiding the sensor assembly to a location within the pipe where the vibrations detected by the sensor assembly are at a maximum; and locating a location of the sensor assembly where the vibrations detected by the sensor assembly is at a maximum.

9. The method of claim 8 wherein the step of guiding the sensor assembly further comprises:
pushing a guide wire that is connected to the sensor assembly into the pipe.

10. The method of claim 9 wherein the step of locating a location of the sensor assembly comprises measuring a length of the guide wire.

11. The method of claim 8 wherein the step of locating a location of the sensor assembly comprises determining a location of an electromagnetic signal transmitter attached to the sensor assembly with a receiver.

12. The method of claim 11 further comprising adding pressure within the pipe.

13. The method of claim 12 wherein the step of adding pressure within the pipe comprises connecting a pressure rig to the pipe.

* * * * *